(12) United States Patent
Overaker et al.

(10) Patent No.: US 6,241,732 B1
(45) Date of Patent: Jun. 5, 2001

(54) BIOCOMPATIBLE ABSORBABLE RIVETS AND PINS FOR USE IN SURGICAL PROCEDURES

(76) Inventors: David W. Overaker, 32 West St., Annandale, NJ (US) 08801; Shawn T. Huxel, 3297 Ridgeway Rd., Lakehurst, NJ (US) 08733; Kevin Cooper, 15 Arrighi Dr., Warren, NJ (US) 07059; Dennis D. Jamiolkowski, 20 Fawnridge Dr., Long Valley, NJ (US) 07853

( * ) Notice: Subject to any disclaimer, the term of this patent is extended or adjusted under 35 U.S.C. 154(b) by 45 days.

(21) Appl. No.: 09/185,051

(22) Filed: Nov. 3, 1998

(51) Int. Cl.[7] ..................................................... A61B 17/56
(52) U.S. Cl. ................................................................ 606/72
(58) Field of Search ................................. 606/75, 69, 72, 606/272, 68; 623/16

(56) References Cited

U.S. PATENT DOCUMENTS

| | | |
|---|---|---|
| 4,011,602 * | 3/1977 | Rybicki et al. .................. 606/62 |
| 4,414,967 | 11/1983 | Shapiro . |
| 4,590,928 | 5/1986 | Hunt et al. . |
| 4,738,255 | 4/1988 | Goble et al. . |
| 5,102,421 | 4/1992 | Anspach, Jr. . |
| 5,167,665 | 12/1992 | McKinney . |
| 5,236,438 | 8/1993 | Wilk . |
| 5,268,001 | 12/1993 | Nicholson et al. . |
| 5,314,989 | 5/1994 | Kennedy et al. . |
| 5,326,205 | 7/1994 | Anspach, Jr. et al. . |
| 5,480,403 | 1/1996 | Lee et al. . |
| 5,489,210 * | 2/1996 | Hanosh ................................ 606/72 |
| 5,501,695 | 3/1996 | Anspach, Jr. et al. . |
| 5,713,903 | 2/1998 | Sander et al. . |
| 5,720,753 | 2/1998 | Sander et al. . |
| 5,725,529 | 3/1998 | Nicholson et al. . |
| 5,782,865 * | 7/1998 | Grotz ................................. 606/232 |

FOREIGN PATENT DOCUMENTS 0 611 557   8/1994  (EP) .

* cited by examiner

Primary Examiner—Michael Buiz
Assistant Examiner—(Jackie) Tan-Uyen T. Ho

(57) ABSTRACT

A bioabsorbable rivet and pin fastening device that may be used for attachment of a fixation plate to bone is described herein. The rivet having a head that is mechanically connected to two or more legs that extend generally distally from the head. The pin being radially compressible and less compliant than the legs of the rivet. The pin when inserted into the rivet will contact the internal surface of said legs to apply force on said legs in a direction perpendicular to the central axis to frictionally engage with the adjacent bone.

13 Claims, 4 Drawing Sheets

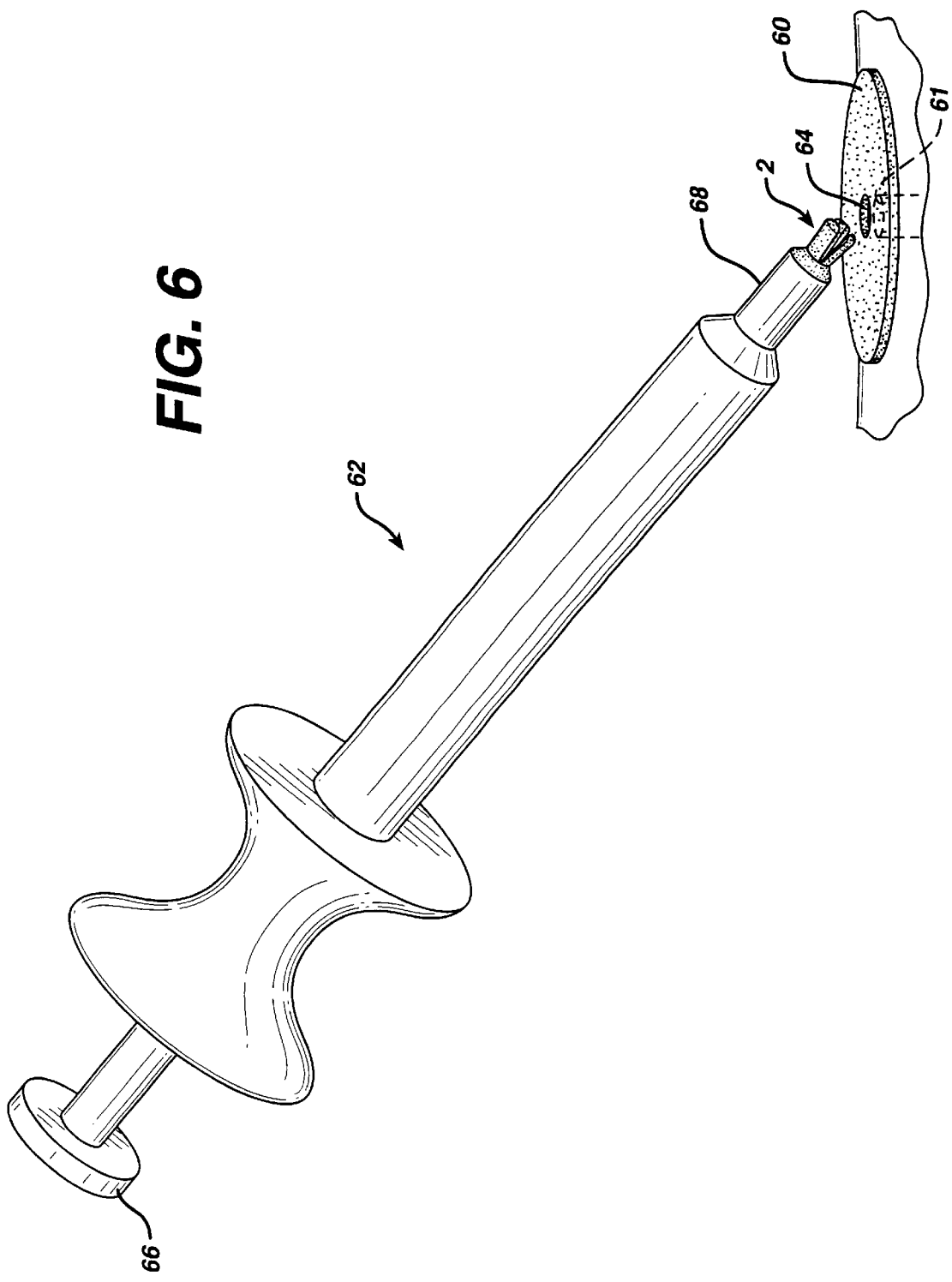

BIOCOMPATIBLE ABSORBABLE RIVETS AND PINS FOR USE IN SURGICAL PROCEDURES

FIELD OF THE INVENTION

The field of art to which this invention relates is surgical devices, in particular absorbable orthopedic fasteners. Specifically, absorbable polymer rivets and pins for use in the fixation of bone, especially hard tissue of the cranium or face, for plastic or reconstructive surgical procedures.

BACKGROUND OF THE INVENTION

There are currently a variety of metallic fasteners available for attaching bone plates to fracture and surgery repair sites; spinal, cranial, and maxillo-facial plates have all been fastened using metal screws. The disadvantage of metal devices is that they are permanent and may need to be removed through a second surgical procedure. If they remain in the body, tissue atrophy and subsequent loosening of the device may occur.

Synthetic absorbable biocompatible polymers are well known in the art. Such polymers are typically used to manufacture medical devices, which are implanted in body tissue and absorb over time. Synthetic absorbable biocompatible aliphatic polyesters include homopolymers, copolymers (random, block, segmented and graft) of monomers such as glycolic acid, glycolide, lactic acid, lactide(d, 1, meso and mixtures thereof), $\epsilon$-ccaprolactone, trimethylene carbonate and p-dioxanone. Numerous U.S. Pat. Nos. describe these polymers including 5,431,679; 5,403,347; 5,314,989; 5,431,679; 5,403,347; and 5,502,159.

With the advent of absorbable polymers has come a new generation of fasteners (screws, pins, etc.) that are designed to be gradually absorbed by the body as their functional use declines. Devices made of an absorbable material have the advantage that they remain only for the period of time required for healing.

There are a number of orthopedic rivets disclosed in the prior art.

U.S. Pat. No. 5,167,665 describes a blind rivet with a head on its proximal end and a center mandrel which has a bead or head distal to the head of the rivet. The combination is inserted into a predrilled hole in the bone and is secured under the cortical layer of bone by pulling the center mandrel proximally, thereby collapsing the bead to form a second head that remains under the cortical layer.

U.S. Pat. Nos. 5,268,001 and 5,725,529 describe a flexible sleeve member and an elongated element where the elongated element has an outer diameter that is greater than the inner diameter of the sleeve. The sleeve is inserted into a predrilled hole in the bone. Then the element is inserted into the sleeve forcing it outwardly to secure it to the bone.

U.S. Pat. Nos. 5,326,205 and 5,501,695 describe a fastener adapted to expand into bone. The fastener has a tubular body with a longitudinal opening with a head proximally and members that extend along its body distally. A puller with a head at its distal end is inserted into the tubular body. The assembly is inserted into a predrilled hole in the bone. When the puller is moved proximally, it compresses the members on the tubular body, crimping them so that the members engage the bone. The puller is then broken off at the head of the tubular body, leaving the device secured in the bone.

U.S. Pat. No. 5,480,403 describes a suture anchor that includes a rivet that has radially flexible legs proximally and a setting pin with a sharp tip on its end distal to the flexible legs of the rivet and a suture tied to its proximal end. The rivet and pin are inserted into a predrilled hole. The hole is drilled deeper than the depth of the rivet/pin to accommodate the pin since the pin is initially inserted beyond the distal end of the rivet. The pin is then pulled proximally, expanding the proximal legs of rivet which then engage the bone.

In another embodiment of U.S. Pat. No. 5,480,403, the suture anchor has a rivet and pin where the rivet has legs that extend distally. The rivet and pin are inserted into a predrilled hole. When the pin is pulled proximally, the rivet legs, being tapered such that the inner diameter of the rivet is less as one moves proximally towards the head of the rivet, radially expand to secure the suture anchor to the bone surface as the pin is pulled proximally. U.S. Pat. Nos. 5,713,903 and 5,720,753 describe a fastener having expanded legs at its distal end and a pin with a flared distal end set in a central bore at a depth greater than the length of the fastener legs. When the pin is moved proximally, the flared end of the pin expands the legs of the fastener to secure it to the bone. The pin is then detached at a notch at the head of the fastener. This fastener is specifically for securing soft tissue to bone.

These patents relate to devices which are inserted into a hole and then deployed by driving a member upwards, or proximally, through or into a radially flexible portion of the device. This requires that the hole be deeper than the depth of the deployed device in order to leave enough room to fully insert the device before deployment. Such designs are undesirable for surgical applications where only a thin layer of bone is available for attachment or it is not possible to drill beyond the depth of the thin bone layer for fear of damaging underlying soft tissues, such as in cranial and maxillo-facial surgical procedures. In such cases, the required length of the fastener for adequate fastening strength is very close to the total thickness of the bone.

U.S. Pat. No. 4,590,928 describes an anchor consisting of an elongated cylindrical body with a tapered coaxial channel and radially flexible legs and a pin insertable into the end having the head, the proximal end. The body is placed into a hole formed in bone and the pin is inserted into the channel to expand the legs radially into the surrounding bone. The body and pin are of biocompatible material and the body contains carbon fibers embedded in and extending longitudinally along its interior. Since carbon fibers are not absorbed by or resorbed within the body, this fastener is only partially absorbable.

This patent, U.S. Pat. No. 4,590,928, describes a fastener having a solid pin. It is well known that the material properties, such as Young's modulus of elasticity and the material yield stress, of bone tissue change significantly with age and vary significantly among individuals of the same age and sex. Having a solid pin therefore limits the fastening ability of the device since the pin cannot deform if the surrounding bone is so stiff that the legs cannot expand radially outwards.

In such a case where the surrounding bone is stiffer than that for which the device was designed and the pin is solid, the large force required to drive the rigid pin into the tapered hole will be such that either the legs will be deformed and rendered useless or the pin will be crushed. A radially compressible or flexible pin that could deform radially inwards to fit the internal passage under high insertion load conditions would give the fastener better performance over a wider range of bone material properties.

Therefore, what is needed in the art is a novel absorbable fastener for cranial, maxillo-facial, and other reconstructive surgical applications in which the fastener is inserted into a hole having the same depth as the fastener and is deployed by driving a radially compressible member downwards, or distally, into a flexible body of the fastener from above. The current invention discloses such a device.

SUMMARY OF THE INVENTION

The invention disclosed is a biocompatible bioabsorbable rivet and pin fastener comprising: (1) a biocompatible rivet having a head with a proximal end and a distal end and a central axis, the head having an internal passage extending from the proximal to the distal end of the head that is substantially parallel to the central axis of the head, the distal end of the head being mechanically connected to two or more legs that extend generally distally from the head and have an internal surface that faces the central axis, and (2) a biocompatible pin having a radially compressible cross-section that is less compliant than the legs of the rivet which is adapted to be inserted into the internal passage of the rivet and which as advanced from the proximal end toward the distal end of the head of the rivet will contact the internal surface of said legs to apply force on said legs in a direction substantially perpendicular to the central axis.

The pin may include a circumferential notch or rib located on the lateral surface of the pin. The notch or rib on the pin surface would mate with a circumferential rib or notch on the inner surface of the internal channel passing through the body. This would provide a means of locking the pin in position to prevent axial migration of the pin after full insertion of the pin.

The pin may be: 1) a separate body or 2) integral with the body through a breakable connection such that the downward driving force would detach the pin from the body and then drive the pin distally into the body.

Another advantage of the disclosed design is that the pin has flexible members, which are less compliant, or stiffer, than the flexible legs of the body. The pin will therefore be stiff enough to expand the legs of the body radially outwards when the device is deployed in bone with average material properties, for which the device would be designed, but also will have enough compliance to fold inwards when the device is deployed in very stiff bone in which the legs of the body cannot expand outwards.

The foregoing and other features and advantages of the invention will become more apparent from the following description and accompanying examples.

BRIEF DESCRIPTION OF THE DRAWINGS

FIG. 6 is a perspective view of an applier for the rivet and pin fastener.

DETAILED DESCRIPTION OF THE INVENTION

Figure 1:
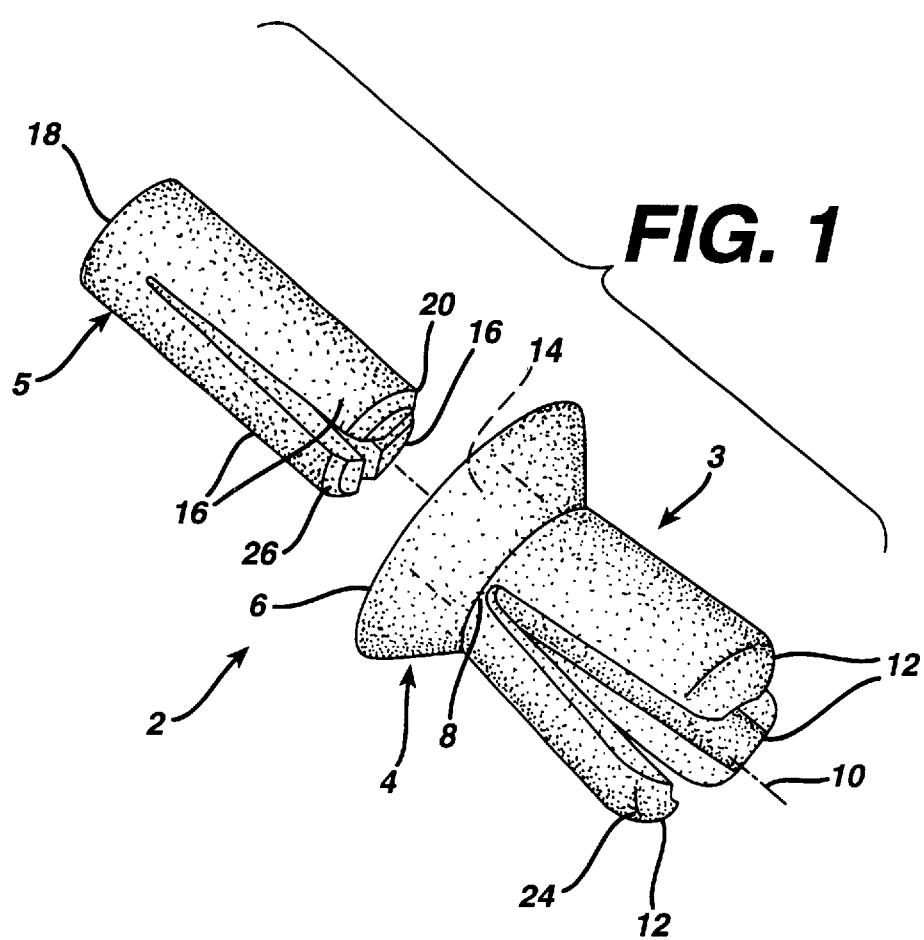
FIG. 1 is a perspective view of one embodiment of the biocompatible, absorbable rivet and pin of the present invention.
Figure 2:
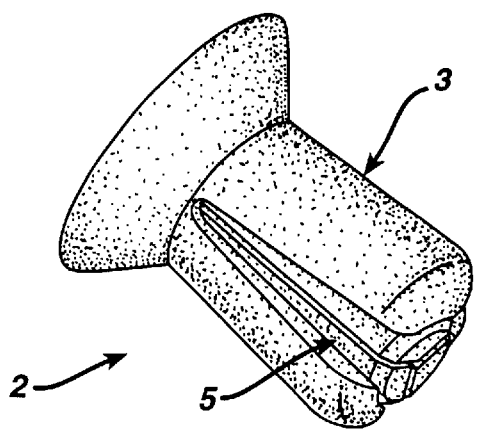
FIG. 2 is a perspective view of the rivet with the pin inserted into the internal passage of the head.

One embodiment of the rivet and pin fastener of the present invention is illustrated in FIG. 1. The rivet and pin fastener 2 is comprised of the rivet 3 and the pin 5. The rivet is made up of the head 4 and at least two legs 12 that are attached to the distal end 8 of the head. The proximal end 6 of the head has an internal passage 14 that is substantially parallel to the central axis of the head 10. The head 4 preferably will expand in diameter from the distal to proximal ends to provide a surface for securing a orthopedic devices to bone upon deployment of said fastener. The pin 5 is radially compressible, which means that the cross-sectional diameter of at least a portion of the pin may be reduced if sufficient radial force is applied to the pin. One embodiment of the pin 5 has at least two distal radially flexible members 16 that are jointed together at junction 18. The rivet and pin fastener is deployed by advancing the insertion end of the pin into the internal passage 14 in the proximal end 6 of the rivet 4. The insertion end 20 of the pin is then advanced toward the distal end 8 of the head 4. As the pin 5 is advanced, the insertion end 20 of the pin will contact the legs 12 of the rivet and exert a force generally perpendicular to the central axis 10 of the rivet 4. The flexible members 16 of the pin 5 are designed to flex rather than cause the flexible legs 12 of the rivet 4 to break or separate from the head 4 as the legs expand outwards to frictionally engage with the adjacent bone.

The flexible legs 12 in the rivet preferably have a geometry, such that the legs 12 increase in thickness extending distally from the connection to the head 4. This feature enables the legs 3 to be forcibly expanded outwards when the straight pin 5 is driven into the internal passage 14. In such a case where the legs 12 increase in thickness extending distally from the connection to the head, the fastener has enhanced anchoring properties when deployed because the outside diameter of the rivet at the distal portion of the legs 12 is larger than the outside diameter of the rivet at the distal end of the head where the legs 12 attach. The legs 12 are therefore expanded outwards beyond the initial hole diameter created in the dense surface layer of bone, the cortex. The legs 12 may also have a chamfered or rounded leading edge 24 to improve the ease of insertion of body into a hole. Likewise, the pin 5 may have a chamfered or rounded leading edge 26 to improve ease of insertion of the pin 5 into the internal passage 14 in the rivet 4. The rivet may also have a chamfered inner surface to allow removal of the device, if necessary, with an applier after it has been set in place.

The pin 5 has radially flexible members 16 at its distal end. In the preferred embodiment, the flexible members 16 of the pin 5 are less compliant, or stiffer, than the flexible legs 12 of the rivet 4. This results in a pin 5 with less structural compliance, or greater structural stiffness, than that of the rivet 4 at the distal end of the device. Insertion of the pin 5 into the internal passage 14 of the rivet 4 will result in radial expansion of the legs 12 of the rivet 4 and radial compression of the members 16 of the pin 5. Since the total stiffness of the members 16 of the pin are greater than the total stiffness of the legs 12 of the rivet 4, the resultant radial force will always be outward to frictionally engage the legs 12 of the rivet 4 with the surrounding bone. However, to prevent the pin 5 from shearing or deforming the legs 12 to the point that the legs will cease to effectively frictionally engage the surrounding bone, at least a portion of the pin 5 will radially compress at a threshold value less that the force which would substantially damage the legs 12.

In another embodiment of the present invention, the surface 28 of the passage 14 has a circumferential notch 30 which mates with a circumferential rib 32 on the lateral surface 31 of the pin 5. Conversely, in another embodiment of the present invention, the surface of the channel 28 may have a circumferential rib which mates with a circumferential notch on the lateral surface of the pin 5. Both embodiments provide a locking means for the inserted pin to prevent axial migration of the pin after insertion. Additionally, this embodiment can easily provide a tactile and/or audio feedback to alert the surgeon that the pin has been locked into place in the rivet.

Figure 3:
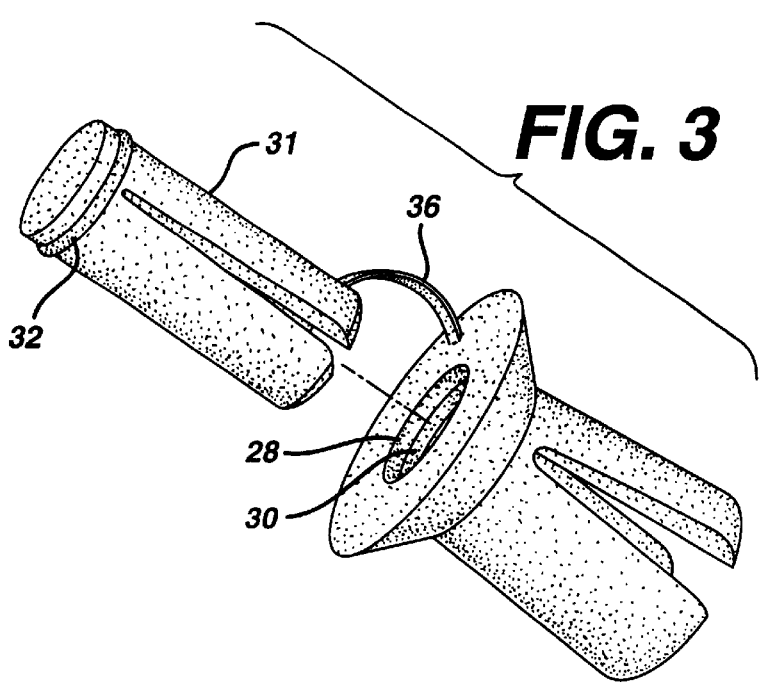
FIG. 3 is a perspective view of an alternative embodiment of the present invention wherein a locking mechanism is present.

In another embodiment of the present invention illustrated in FIG. 3, the rivet 4 and the pin 5 are attached by a thin material connection 36 within the head 4 to form a one-piece device. Once the device is inserted into a hole in bone, a driving force applied to the pin would break the material connection and then drive the pin into the body to deploy the fastener.

Figure 4:
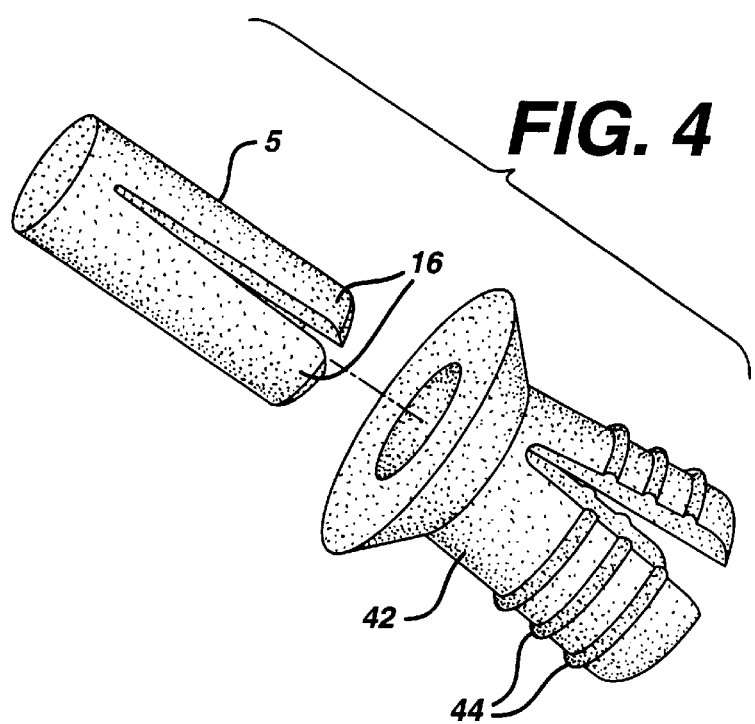
FIG. 4 is a perspective view on another alternative embodiment of the present invention wherein ribs are provided on the legs of the rivet to insure engagement of the rivet with surrounding tissue when it is deployed.

In another embodiment of the present invention illustrated in FIG. 4, the outside lateral surfaces 42 of the legs 12 have one or a number of ribs 44 and/or protrusions that embed into the adjacent bone upon deployment of the fastener in order to increase the fastening strength of the device.

Figure 5:
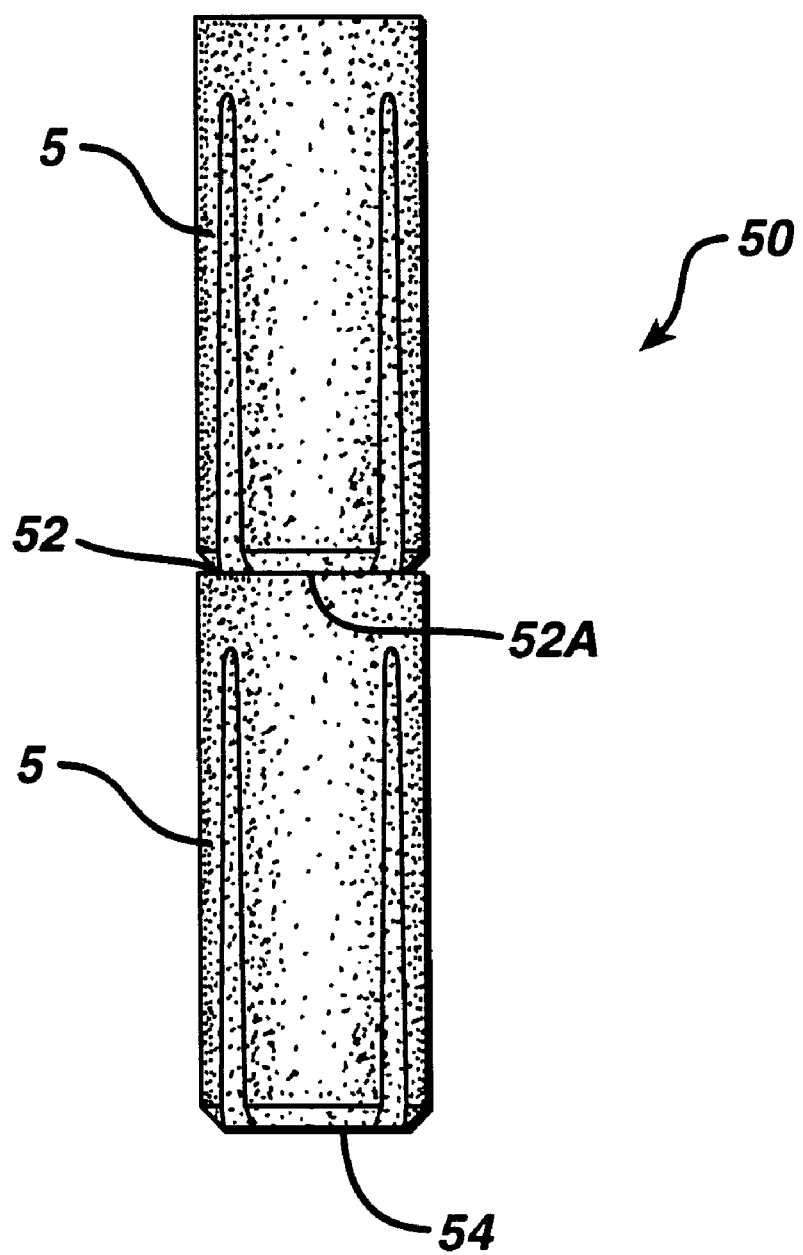
FIG. 5 is a perspective view of an alternative embodiment of the pin.

In another embodiment of the present invention illustrated in FIG. 5, the pin 5 could be part of a continuous rod 50 of pins 5, which are separated by the round or chamfer 52 on the leading edge of the pin 5. A driving force would be applied to the continuous rod 50 to drive the distal end of the rod 54 into the rivet 4 until the insertion end of the pin 5 is fully engaged with the rivet 4. The distal pin is then detached from the rod 50 to break the connection 52 by applying sufficient bending force to the rod or by cutting at the connection 52 thereby generating a new distal end 52A. The continuous rod would therefore be used to deploy a number of rivets.

Also disclosed is a method of applying the fastener 2 as shown in FIG. 6. After the surgeon has drilled a hole 61 in the bone at the location where a plate 60 or other device will be fastened, the rivet and pin are which have been loaded in applier 62. The rivet 4 is then inserted through the plate hole 64 into hole 61. The pin 5 is driven into the rivet 4 by applying a downward force on the plunger 66 of the applier 62. The process is repeated as needed until adequate holding power is obtained for the plate 60.

Suitable materials from which the fastener may be formed include biocompatible polymer selected from the group consisting of: aliphatic polyesters; polyorthoesters; polyanhydrides; polycarbonates; polyurethanes; polyamides; polyalkylene oxides; and combinations thereof. The orthopedic fastener of the present invention can also be formed from absorbable glasses or ceramics comprising calcium phosphates and other biocompatible metal oxides (i.e., CaO). The fastener of the present invention can further comprise combinations of absorbable ceramics, glasses and polymers.

In the preferred embodiment, the orthopedic fastener is comprised of aliphatic polymer and copolymer polyesters and blends thereof. The aliphatic polyesters are typically synthesized in a ring opening polymerization. Suitable monomers include but are not limited to lactic acid, lactide (including L-, D-, meso and D,L mixtures), glycolic acid, glycolide, $\epsilon$-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicyclooctane-7-one and combinations thereof. These monomers are generally polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization is typically carried out at a temperature range from about 80° C. to about 240° C., preferably from about 100° C. to about 220° C., until the desired molecular weight and viscosity are achieved.

The polymer blends of the present invention are manufactured in a conventional manner. One method of blending the homopolymers and copolymers, prepared as described above, is to individually charge the polymers into a conventional mixing vessel or reactor vessel having a conventional mixing device mounted therein, such as an impeller or equivalents thereof. Then, the polymers and copolymers are mixed at a temperature of about 100° C. to about 230° C., more preferably from about 160° C. to about 200° C., for about 5 to about 90 minutes, more preferably for about 10 to about 45 minutes, until a uniformly dispersed polymer blend is obtained. Then, the polymer blend is further processed by removing it from the mixing device, cooling to room temperature, grinding, and drying under pressures below atmospheric at elevated temperatures for a period of time using conventional apparatuses and processes. Another appropriate method of blending the homopolymers or copolymers is by passing the polymers through a twin screw-extruder with an appropriate mixing zone or zones.

Under the above described conditions, the polymers and blends composed of glycolide, $\epsilon$-caprolactone, p-dioxanone, lactide and trimethylene carbonate will typically have a weight average molecular weight of about 20,000 grams per mole to about 300,000 grams per mole, more typically about 40,000 grams per mole to about 260,000 grams per mole, and preferably about 60,000 grams per mole to about 225,000 grams per mole. These molecular weights provide an inherent viscosity between about 0.5 to about 4.0 deciliters per gram (dL/g), more typically about 0.7 to about 3.5 dL/g, and most preferably about 1.0 to about 3.0 dL/g as measured in a 0.1 g/dL solution of hexafluoroisopropanol (HFIP) at 25° C. Also, it should be noted that under the above-described conditions, the residual monomer content would be less than about 5 weight percent.

Articles such as absorbable fastener medical devices of the present invention are molded from the polymers and blends of the present invention by use of various injection and extrusion molding equipment equipped with dry nitrogen atmospheric chamber(s) at temperatures ranging from about 100° C. to about 230° C., more preferably 140° C. to about 200° C., with residence times of about 1 to about 20 minutes, more preferably about 2 to about 10 minutes. The preferred device is an orthopedic rivet fastener. The preferred device should be molded with the rivet having the legs 12 oriented in the an expanded position (the position that the legs will be expanded to when the pin in place). Molding the rivet with the legs expanded will tend to reduce the stress at the junction of the legs 12 with the head 4 when the legs are expanded. Reducing the stress at this junction should extend the useful life of the rivet and pin fastener after implantation.

In another embodiment of the present rivet invention, the polymers and blends can be used as a drug delivery matrix. To form this matrix, the polymer would be mixed with a therapeutic agent. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; analgesics and analgesic combinations; anti-inflammatory agents; hormones such as steroids; bone regenerating growth factors; and naturally derived or genetically engineered proteins, polysaccharides, glycoproteins, or lipoproteins.

Matrix formulations may be formulated by mixing one or more therapeutic agents with the polymer. The therapeutic agent, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001% to about 70%, more typically about 0.001% to about 50%, most typically about 0.001% to about 20% by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Following this or similar procedures, those skilled in the art will be able to prepare a variety of formulations.

In another embodiment of the present rivet invention, a biocompatible dye could be added to the polymer comprising the device during processing in order to make it more visible in the surgical field. Alternatively, the pin and rivet could be color coded to provide a visual feedback to alert the surgeon that the pin has been inserted into the rivet. The rivet and pin combination may also incorporate tactile and/or audio feedback to alert the surgeon that the device has been inserted.

Additionally, radio-opaque markers may be added to the rivet or pin to allow imaging of the rivet and pin fastener after implantation.

The following non-limiting examples are illustrative of the principles and practice of this invention. Numerous additional embodiments within the scope and spirit of the invention will become apparent to those skilled in the art.

EXAMPLES

The examples describe a fastener system that is fabricated from an absorbable polymer or polymer blends and consists of a body with flexible legs and a pin that is inserted into the body to expand the legs.

In the synthetic process, the high molecular weight aliphatic polyesters of the device of the present invention are prepared by a method consisting of reacting lactone monomers via a ring opening polymerization at temperatures of 100° C. to 230° C. for 2 to 24 hours under an inert nitrogen atmosphere until the desired molecular weight and viscosity are achieved.

The polymer blends of the present invention are prepared by individually charging the synthesized aliphatic homo- and co-polyesters into a conventional mixing vessel. The homopolymers and copolymers are mixed at a temperature of 100° C. to 230° C., for 5 to 90 minutes until a uniformly dispersed polymer blend is obtained.

In the examples which follow, the blends, polymers and monomers were characterized for chemical composition and purity (NMR, FT-IR), thermal analysis (DSC), melt rheology (melt stability and viscosity), molecular weight (inherent viscosity), and baseline mechanical properties (stress/strain).

Inherent viscosities (I.V., dL/g) of the blends and polymers were measured using a 50 bore Cannon-Ubbelhode dilution viscometer immersed in a thermostatically controlled water bath at 25° C. utilizing chloroform or HFIP as the solvent at a concentration of 0.1 g/dL.

Several examples will be described in the following few pages. Parts and percentages where used are parts and percentages as specified as weight or moles.

Example 1

Synthesis of a 85:15 (mol/mol) poly(lactide-coglycolide) copolymer

The method described below and utilized in this example is similar to those described in U.S. Pat. Nos. 4,643,191, 4,653,497, 5,007,923, 5,047,048 which are incorporated by reference, and is known to those skilled in the art.

To a flame dried 500 mL 1-neck round bottom flask equipped with an overhead mechanical stirrer and nitrogen inlet, 268 grams (1.86 moles) of L(−) lactide, 38.4 grams (0.330 moles) of glycolide, 0.53 grams ($7 \times 10^{-3}$ moles) of glycolic acid initiator, and 131 microliters of a 0.33 M solution of stannous octoate catalyst are added.

The assembly is then placed in a high temperature oil bath at 185° C. The stirred monomers quickly begin to melt. The low viscosity melt quickly increases in viscosity. Mechanical stirring of the high viscosity melt is continued for a total reaction time of 4 hours.

The 85:15 (mol/mol) poly(lactide-co-glycolide) copolymer is removed from the bath, cooled to room temperature under a stream of nitrogen, isolated and ground. The polymer is then dried under vacuum at 110° C. for 24 hours to remove unreacted monomer. Inherent viscosity using HFIP as a solvent is 1.90 dL/g.

Example 2

Injection Molding a Rivet and Pin of an 85:15 poly(lactide-co-glycolide) copolymer 1.5 Kg of the copolymer as formed in Example 1 is added to a nitrogen purged hopper of a 28 ton Engel injection molder equipped with an 18 mm diameter barrel to form a rivet or pin as shown in FIG. 1. Three heating zones of 200, 190, and 185° C. are employed to melt the polymer as it entered the barrel. A nozzle temperature of 185° C. with an injection pressure of 700 psi and a speed of 2 in/s is used to feed the molten material down the barrel. Each injection will produce a single part in a single cavity mold. A temperature of 45° C. is used in the mold to optimize the stress levels in the part. Using this process two parts are formed per minute.

Example 3

Step-by-Step Process of Fastener Use in Animal Model or for Human Use

Referring to FIG. 6, after the surgeon has drilled a hole 61 in the bone location where a plate 60 or other device must be fastened, the rivet 4 and pin 5 are loaded into the receiver 68 of the applier 62. The rivet 4 is then inserted into the plate hole 64 and the pin 5 is driven into the rivet 4 by applying a downward force on the plunger 66 of the applier 62. The size of the hole the surgeon drills should be modified based on the type of bone and the cross-sectional diameter of the rivet (with the pin in place). The hole that will be drilled in the bone will necessarily be smaller than the diameter of the rivet with the pin in place. However for bone which is of a soft nature (substantially cancellous bone), the hole diameter may be even smaller to increase the frictional engagement of the rivet and pin fastener with the softer bone. For bone which is harder in nature (substantially cortical bone), the hole diameter should be closer to the diameter of the rivet (with the pin in place) to ease the application of the rivet and pin fastener.

We claim:

1. A bioabsorbable biocompatible rivet and pin fastening device comprising:
   (a) a biocompatible rivet having a head with a proximal end and a distal end and a central axis, the head having an internal passage extending from the proximal to the distal end of the head that is substantially parallel to the central axis of the head, the distal end of the head being mechanically connected to two or more legs that extend generally distally from the head and have an internal surface that faces the central axis, and
   (b) a biocompatible pin having a radially compressible cross-section that is less compliant than the legs of the rivet which is adapted to be inserted into the internal passage of the rivet and which as advanced from the proximal end toward the distal end of the head of the rivet will contact the internal surface of said legs to apply force on said legs in a direction perpendicular to the central axis.

2. The bioabsorbable biocompatible rivet and pin fastening device of claim 1 wherein the biocompatible fastener is made from biocompatible aliphatic polyesters.

3. The bioabsorbable biocompatible rivet and pin fastening device of claim 1 wherein the aliphatic polyester is formed from a monomer selected from the group consisting of lactic acid, lactide (including L-, D-, meso and D,L mixtures), glycolic acid, glycolide, ε-caprolactone, p-dioxanone (1,4-dioxan-2-one), trimethylene carbonate, 1,3-dioxan-2-one, p-dioxanone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

4. The bioabsorbable biocompatible rivet and pin fastening device of claim 2 wherein the absorbable polymeric matrix comprises an aliphatic polyester selected from the group consisting of polylactide, polyglycolide, poly-1,4-dioxan-2-one, polytrimethylene carbonate and poly(ε-caprolactone), copolymers and blends thereof.

5. The bioabsorbable biocompatible rivet and pin fastening device of claim 1 wherein the pin has two or more members which are joined.

6. The bioabsorbable biocompatible rivet and pin fastening device of claim 1 wherein the pin has a circumferential notch and the rivet has an internal circumferential rib that may mate and lock the pin in the rivet.

7. The bioabsorbable biocompatible rivet and pin fastening device of claim 1 wherein at least one of the legs of the rivet has a lateral surface and one or more ribs thereon.

8. The bioabsorbable biocompatible rivet and pin fastening device of claim 1 wherein rivet and pin are linked by a detachable connection.

9. The bioabsorbable biocompatible rivet and pin fastening device of claim 2 wherein the rivet contains a therapeutically effective amount of a therapeutic agent selected from the group consisting of antiinfectives, anti-inflammatory agents, proteins, polysaccharides and combinations thereof.

10. The bioabsorbable biocompatible rivet and pin fastening device of claim 2 wherein the rivet contains a therapeutically effective amount of a therapeutic agent selected from the group consisting of analgesics hormones, bone regenerating growth factors, glycoproteins, lipoproteins and combinations thereof.

11. The bioabsorbable biocompatible rivet and pin fastening device of claim 2 wherein the pin contains a therapeutically effective amount of a therapeutic agent selected from the group consisting of antiinfectives, anti-inflammatory agents, proteins, polysaccharides and combinations thereof.

12. The bioabsorbable biocompatible rivet and pin fastening device of claim 2 wherein the pin contains a therapeutically effective amount of a therapeutic agent selected from the group consisting of analgesics hormones, bone regenerating growth factors, glycoproteins, lipoproteins and combinations thereof.

13. A bioabsorbable biocompatible rivet and pin fastening device comprising:
   (a) a biocompatible rivet having a head with a proximal end and a distal end and a central axis, the head having an internal passage extending from the proximal to the distal end of the head that is substantially parallel to the central axis of the head, the distal end of the head being mechanically connected to two or more legs that extend generally distally from the head and have an internal surface that faces the central axis, and
   (b) a biocompatible pin having a radially compressible cross-section that is less compliant than the legs of the rivet which is adapted to be inserted into the internal passage of the rivet and which as advanced from the proximal end toward the distal end of the head of the rivet will contact the internal surface of said legs to apply force on said legs in a direction perpendicular to the central axis wherein the rivet is molded with the legs in substantially the position that the legs would be in with the pin in place.

* * * * *